(12) United States Patent
Koshelev et al.

(10) Patent No.: US 8,026,487 B2
(45) Date of Patent: Sep. 27, 2011

(54) SUPERCONDUCTING SOURCE FOR TUNABLE COHERENT TERAHERTZ RADIATION

(75) Inventors: Alexei E. Koshelev, Bolingbrook, IL (US); Lutfi Ozyuzer, Izmir (TR); Cihan Kurter, Westmont, IL (US); Ulrich Welp, Lisle, IL (US); Wai-Kwong Kwok, Evanston, IL (US); Kenneth E. Gray, Naperville, IL (US)

(73) Assignee: UChicago Argonne, LLC, Chicago, IL (US)

( * ) Notice: Subject to any disclaimer, the term of this patent is extended or adjusted under 35 U.S.C. 154(b) by 749 days.

(21) Appl. No.: 11/963,532

(22) Filed: Dec. 21, 2007

(65) Prior Publication Data

US 2010/0264312 A1 Oct. 21, 2010

(51) Int. Cl.
*G01J 5/02* (2006.01)
(52) U.S. Cl. .................................... 250/341.8
(58) Field of Classification Search .............. 250/330, 250/332, 338.3, 341.8; 505/190, 193
See application file for complete search history.

(56) References Cited

U.S. PATENT DOCUMENTS

| 2002/0074500 A1* | 6/2002 | Mickan et al. | 250/341.8 |
| 2005/0098728 A1* | 5/2005 | Alfano et al. | 250/341.8 |
| 2007/0244012 A1* | 10/2007 | Welp et al. | 505/190 |

* cited by examiner

*Primary Examiner* — Mark R Gaworecki
(74) *Attorney, Agent, or Firm* — Foley & Lardner LLP

(57) ABSTRACT

A system includes a solid state source of THz radiation and a detector. The source of THz radiation may be based on a superconducting material, such as materials containing one or more Josephson junctions (e.g. BSCCO). The source may include a crystal of superconducting material on which a mesa of superconducting material is formed. The resonant coupling between the Josephson oscillations and the fundamental cavity mode of the mesa may lead to synchronization of the Josephson junctions and emission of powerful THz radiation. The mesa may be formed and/or handled such that THz radiation can be emitted by the material without requiring application of an external magnetic field (e.g. the mesa may include a non-uniform compositional gradient, a non-uniform shape, may have radiation non-uniformly applied to the mesa, etc.).

15 Claims, 12 Drawing Sheets

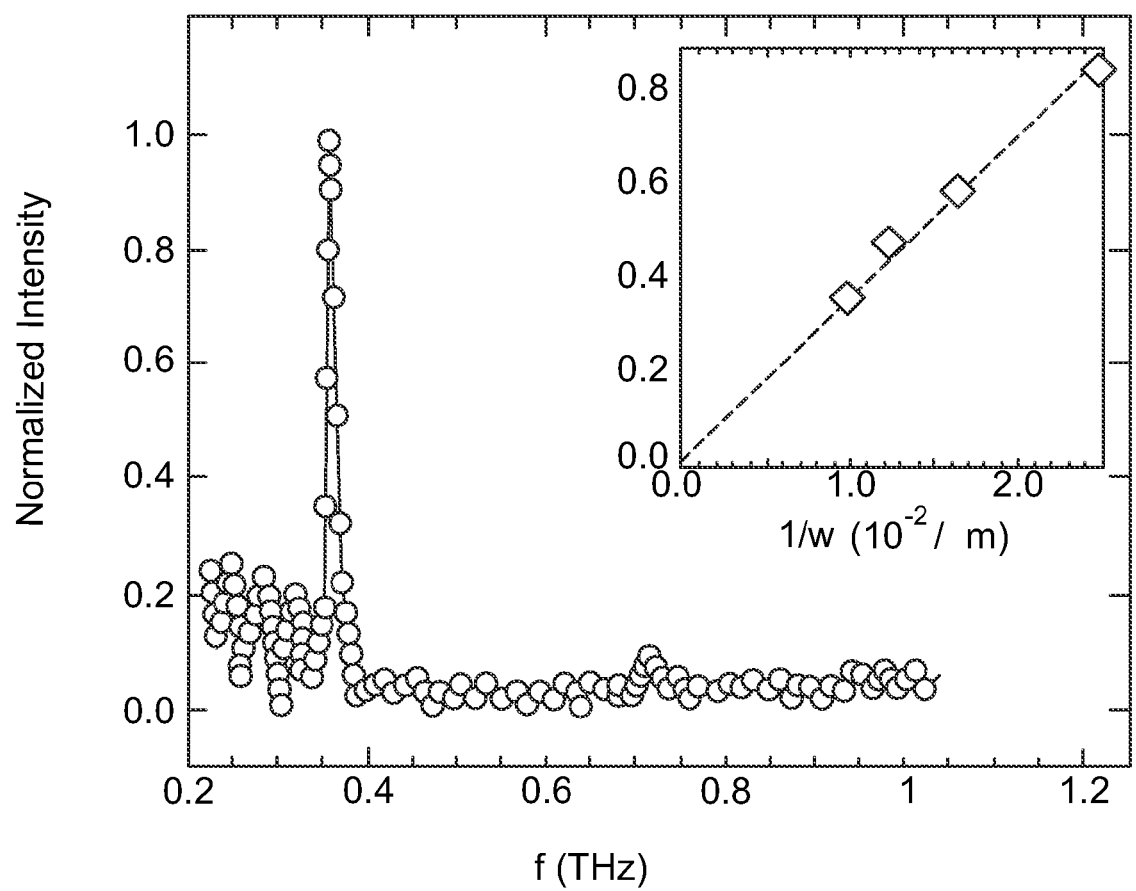
FIG. 7B-I

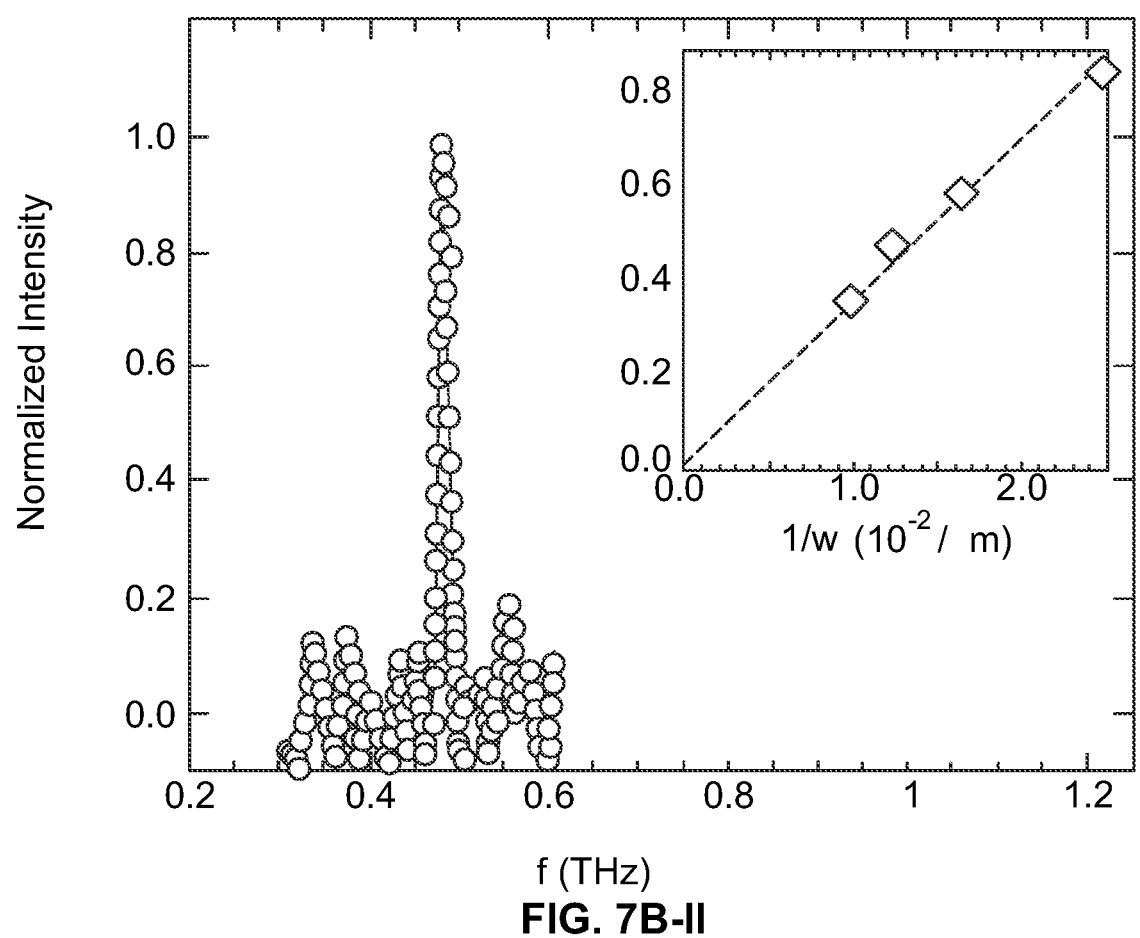
FIG. 7B-II

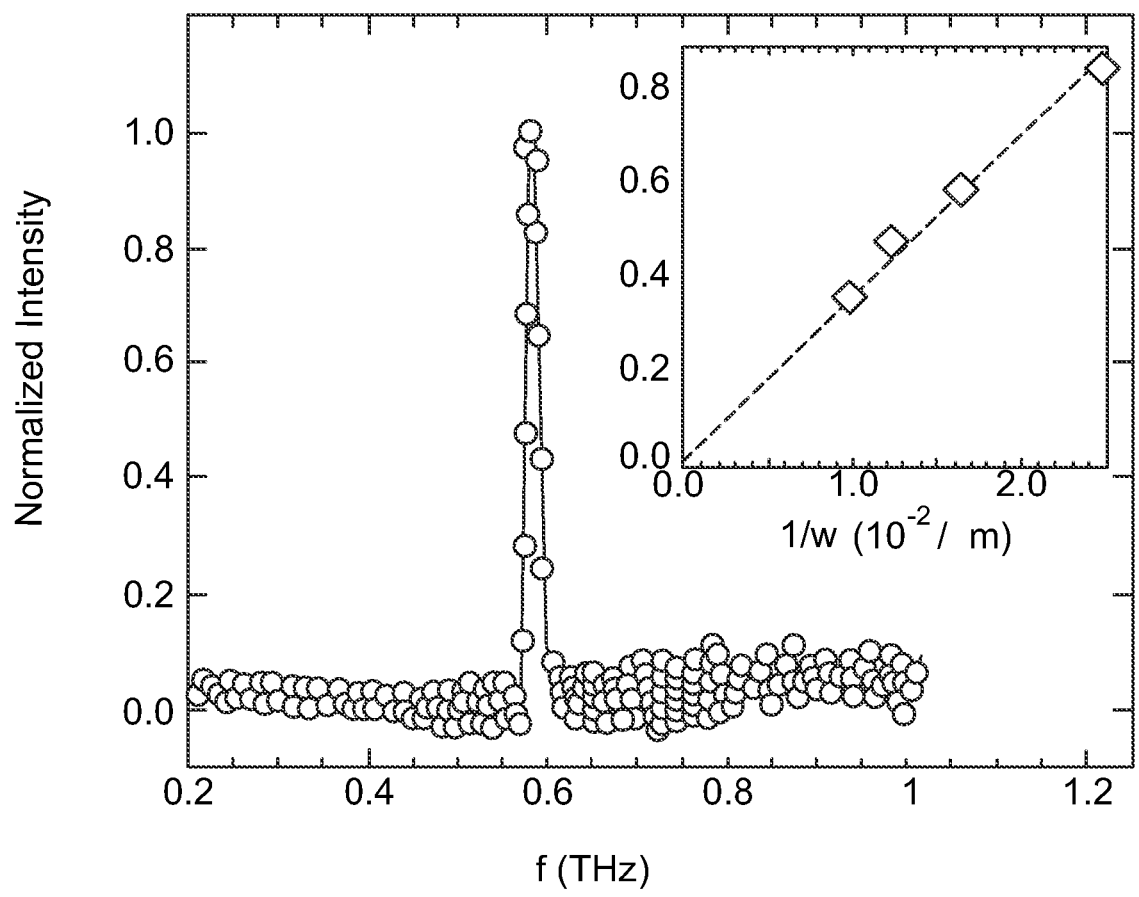
FIG. 7B-III

SUPERCONDUCTING SOURCE FOR TUNABLE COHERENT TERAHERTZ RADIATION

GOVERNMENT INTEREST

The United States Government may have certain rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

BACKGROUND

This application generally relates to the field of Terahertz-based technologies. In particular, the application relates to a new source of Terahertz radiation, methods of manufacturing the new source, and systems incorporating such a source.

The THz-frequency range of the electromagnetic spectrum is frequently defined as ranging from 0.3 to 20 THz (10-666 $cm^{-1}$, 1 mm-15 μm).

The emerging field of terahertz science and technology holds promise in many diverse fields. This diverse range generally derives from two unique properties of THz radiation, its spectral specificity to vibrational and rotational modes of a wide variety of important chemical and biomolecular species, and to its penetrating properties through packaging materials, clothes, plastics, etc.

Ultra-fast laser pumped photoconductive switches, pumped gas lasers, optical difference frequency generation and parametric oscillation, frequency-doubled diodes, and quantum cascade lasers among others are approaches pursued for developing sources of THz-radiation. Progress in this field is blocked by lack of portable, powerful, and tunable radiation sources.

SUMMARY

A system includes a solid state source of THz radiation and a detector. The source of THz radiation may be based on a superconducting material, such as materials containing one or more Josephson junctions (e.g. BSCCO). The source may include a crystal of superconducting material on which a mesa of superconducting material is formed. The mesa may help focus waves contained in the material such that the waves are provided roughly in phase and at about the same frequency. For example, the mesa may be configured such that a Fabry-Perot cavity mode is formed, to which the waves in Josephson junctions of the superconductor may be coupled.

The mesa may be formed and/or handled such that THz radiation can be emitted by the material without requiring application of an external magnetic field. For example, the mesa may include a non-uniform compositional gradient, a non-uniform shape, a means of suppressing superconductivity (e.g. may have radiation non-uniformly applied to the mesa), and/or have some other feature that provides a non-uniform coupling between a current applied to the superconductor and electromagnetic modes of the superconductor.

Many embodiments of the present invention relate to methods and/or apparatus to synchronize substantially all and/or all junctions in the stack of intrinsic Josephson junctions into coherent in-phase oscillations. In some embodiments of the invention, the stack of junctions may be configured such that a Fabry-Perot cavity mode can be formed. The voltage across the stack may be adjusted in such a way that the oscillation frequency of the junctions coincides with the frequency of the cavity mode. Under this resonance condition the oscillations in the Josephson junctions may couple to the cavity mode, and as a consequence, may oscillate in phase at substantially the same (e.g. the same) frequency of the cavity mode. Then, the electromagnetic waves from each junction may add up coherently resulting in sizable emission power.

One aspect of some embodiments of the invention relates to the coupling of the Josephson oscillations and the cavity mode. In order to achieve efficient coupling and thereby feed energy efficiently into the cavity mode, the stack may include a non-uniform composition or structure, may include a non-uniform shape, may have radiation non-uniformly applied to it, or may have a non-uniform temperature.

In many embodiments, the mesa may be formed and/or handled such that THz radiation can be emitted by the material without requiring application of an external magnetic field.

Another aspect of some embodiments of the invention relate to the emission of THz-radiation with tunable frequency. For mesas that may have non-rectangular cross-sections or other patterning the emission frequency may be tuned by changing the applied voltage around the resonance condition.

Various aspects of the invention are described hereinafter; and these and other objects of improvements are described in detail hereinafter, including the drawings described in the following section.

BRIEF DESCRIPTION OF THE DRAWINGS

FIGS. 7A and 7B illustrate the spectral analysis of the emitted radiation from several exemplary mesas using (7A) the transmission cut-off through parallel-plate filters and (7B) direct far-infrared spectra. The inset shows the proportionality of the emission frequency and the inverse mesa width;

DETAILED DESCRIPTION OF EXEMPLARY EMBODIMENTS

Figure 1:
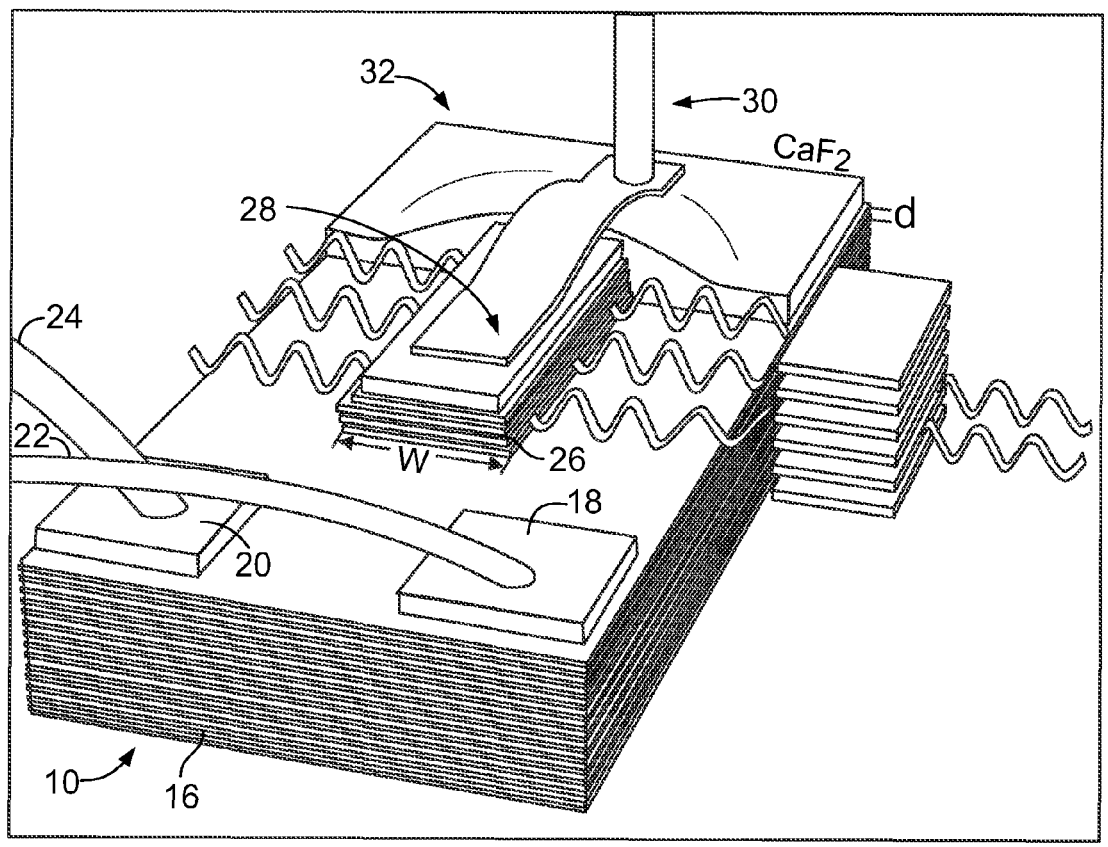
FIG. 1 is an exemplary arrangement for a source of THz radiation.

An alternative approach for providing THz radiation is based on the superconducting Josephson effect that occurs between layers of superconducting materials that are separated by thin insulating non-superconducting materials. An alternating electromagnetic wave (referred to as Josephson plasma waves in what follows) whose frequency is proportional to the voltage difference applied between the superconducting layers arises in the insulating layer. A voltage of 1 mV corresponds to a frequency of 0.483 THz. The highly anisotropic $CuO_2$-based high-temperature superconductors, such as the $Bi_2Sr_2CaCu_2O_8$, $Bi_2Sr_2Ca_2Cu_3O_{10}$ and $Tl_2Ba_2CaCu_2O_8$ derived superconductors, are composed of superconducting $CuO_2$ layers separated by insulating layers, thereby forming stacks of intrinsic Josephson junctions. Extensive numerical simulations indicated that the high packing density of such atomic scale junctions could form the basis for efficient sources of THz-radiation. However, the key requirement for producing useful radiation from such stacks of intrinsic junctions, namely achieving synchronization of the high-frequency oscillations of all the junctions in the stack, has so far been a major challenge preventing the realization of a useful THz-source.

A tunable and portable source of Terahertz (THz) radiation can be made by extracting radiation from oscillating waves within a body. The waves may be electromagnetic waves that may arise due to the application of an electrical current (e.g. to the body). The body may be formed using one or more materials possessing one or more Josephson junctions (e.g. one or more intrinsic Josephson junctions) such as $Bi_2Sr_2CaCu_2O_8$ (BSCCO, bismuth strontium calcium copper oxide).

THz radiation may be extracted from the body that consists of a multilayer structure. The multilayer structure may be formed of multiple layers of one or more materials and may contain one or more Josephson junctions (e.g. intrinsic Josephson junctions). In some embodiments, the multilayer structure may be configured to create a Fabry-Perot cavity mode to which the waves in the junctions may be coupled.

In some embodiments, the radiation produced by the Josephson junctions may be harnessed with the application of substantially no magnetic field (i.e. a field of less than 50 μT such as 0 μT).

In some of these embodiments, the Josephson junction component may include an asymmetrical structure (such as but not limited to an asymmetrical cross-section, a non-uniform composition or structure, a non-uniform shape, a radiation non-uniformly applied to it, or a non-uniform temperature) which may induce an efficient coupling between the current and the electromagnetic modes.

The portable radiation source may be used in one or more analytical applications such as medical diagnostics, security screening, space exploration, environmental monitoring, manufacturing evaluation, and/or pharmaceutical evaluation. The portable radiation source may be used in conjunction with a detector that provides data relating to THz waves that have been in contact with (e.g. passed through, scattered by, etc.) a subject of interest, and a processor coupled to the detector to analyze the data provided by the detector.

Referring to FIG. 1, a Josephson junction is an arrangement of two superconductors linked by an insulating (generally thin) barrier. A property of Josephson junctions is generally to generate high-frequency electromagnetic fields having a frequency proportional to an applied voltage. This typically makes it possible to fabricate coherent tunable high-frequency sources 10. However, using Josephson junctions as a source of high-frequency electromagnetic fields is complicated by the need to synchronize all junctions in the array to oscillate in phase. One method of synchronizing junctions according to some embodiments is to couple them to the same electronic resonance circuit.

One material providing a Josephson junctions is BSCCO; BSCCO generally exhibits the intrinsic Josephson effect—BSCCO can be regarded as stack of intrinsic Josephson junctions in which the superconducting $CuO_2$ planes are separated by insulating Bi—Sr—O layers. The intrinsic Josephson effect in BSCCO may enable the fabrication of arrays (e.g. one-dimensional arrays) of a very large number of closely-packed substantially identical junctions. The array of junctions may be formed in stacked structure 26 (e.g. mesas). The stacked structure 26 may be sculpted onto single crystals 16.

A radiation source 10 may be configured such that multiple junctions (e.g. substantially all and/or all junctions) in such a stack may be configured to oscillate at essentially the same (e.g. the same) frequency and essentially in phase (e.g. in phase). This uniformity may produce strong coherent electromagnetic emission with a total power scaling as the square of the number of junctions. In some embodiments, the source 10 provides a power output (e.g. far field radiation power) of at least about 20 nW, at least about 30 nW, at least about 40 nW, at least about 50 nW, at least about 100 nW, at least about 250 nW, at least about 500 nW, at least about 1 μW, at least about 10 μW, at least about 100 μW, at least about 500 μW, at least about 1 mW, and/or at least about 1.5 mW. In some embodiments, the source 10 provides a power output (e.g. far field radiation power) of less than about 50 mW, less than about 35 mW, less than about 20 mW, less than about 10 mW, less than about 1 mW, less than about 500 nW, less than about 250 nW, less than about 100 nW, less than about 75 nW, and/or less than about 50 nW.

In some embodiments, such synchronization may be facilitated by coupling of the junctions to resonant modes in an external cavity (e.g. a microwave cavity) and/or in a cavity formed by the stacked structure 26 (e.g. mesa) itself. In some of these embodiments, the synchronization is primarily (more than 50%) and/or essentially (more than 90%) synchronized within the stacked structure 26 itself.

In some embodiments, electromagnetic waves inside large-area multilayer structures 26 (e.g. mesas) may tend to propagate as Josephson plasma modes. The in-plane velocity of these modes may depend on the out-of-plane wave-vector, with the highest velocity corresponding to the in-phase mode (all junctions oscillate in-phase) and the lowest to the anti-phase mode in which neighboring junctions oscillate out-of-phase. Furthermore, for all such modes, multiple reflections at the side faces of the structure 26 may lead to a standing wave pattern (e.g. a Fabry-Perot type cavity resonance).

Generally, waves that are out of phase may cancel each other, and thereby reduce the amount of measurable emissions outside the surface of the THz radiation producing body. In some embodiments, the stacked structure is configured to reduce the extent of cancellation due to out of phase waves at a surface of the stacked structure 26.

In particular, in some embodiments, electromagnetic fields residing in the Josephson junctions may be converted into coherent, polarized high-frequency radiation (e.g. THz radiation).

In some embodiments, the waves within the Josephson junctions may be synchronized to be in essentially the same phase by coupling the waves to a Fabry-Perot cavity mode. This synchronizations may result in an available electro-magnetic energy that increases quadratically with the number of junctions rather than linearly as is observed for uncorrelated junctions. In some embodiments, this synchronization, at resonance, may cause energy to be pumped efficiently into this synchronized mode, enhancing its intensity by a factor equal to the quality factor of the cavity.

Referring to FIG. 1a, in some embodiments, the cavity is formed by the BSCCO mesa (structure 26) itself, and resonance may tend to occur when the width, W, of the mesa equals an integer multiple of the half-wavelength of the Josephson plasma waves: $W = m\lambda/2$.

In some embodiments, the electro-magnetic waves described above may be excited essentially without (e.g. without) external application of a magnetic field. This is contrary to many teachings in the art from prior approaches which rely on operating the Josephson junctions in a magnetic field that is applied parallel to the junction in order to generate high-frequency electromagnetic radiation.

In some embodiments, the electro-magnetic waves described above may be excited essentially without (e.g. without) external application of a magnetic field. This is contrary to many teachings in the art from prior approaches that the use of Josephson junctions as a source of electromagnetic radiation, which approaches rely on operating the Josephson junction in a magnetic field that is applied parallel to the junction.

An analysis of the fundamental symmetry properties of a device such as shown in FIG. 1 indicates that a uniform current flowing perpendicular to the junctions cannot excite the resonant cavity modes. Symmetry may be broken in any number of ways to enable the excitation of the resonant cavity modes in zero applied magnetic field. These methods for breaking symmetry may be designed to create the most efficient transfer of energy into the resonant cavity mode.

One method for creating a structure 26 lacking symmetry may be to introduce compositional gradients (e.g. of BSCCO) in the structure 26. These compositional gradients may induce a non-uniform critical current density across the width of the mesa. For example, the superconducting properties of BSCCO ($T_c$, $J_c$...) are generally believed to strongly depend on its oxygen content. Thus, controlled annealing in an oxygen atmosphere may be used to establish a critical current density that is higher near one side face of a structure 26 than near the opposite face of the structure 26. Similarly, the critical current near the side-faces may be higher or lower than near the center of the mesa.

A second method for creating a structure 26 lacking symmetry may be to form the structure 26 in an asymmetric shape (e.g. cross-section). For example, the shape of a mesa structure may include a trapezoidal shape (cross-section) and/or a different non-rectangular shape (cross-section). The asymmetrical shape may induce an asymmetric current flow and/or an asymmetric reflection coefficient at the side faces.

A third method for creating a structure 26 lacking symmetry may be to provide an asymmetric critical-current distribution. For example, superconductivity may be deliberately suppressed on at least one side of the structure 26 such as by irradiating that side(s) by an electron beam, by a proton beam, and/or by ion implantation.

Any of these methods for creating a lack of (e.g. breaking) symmetry may be used alone or may be used in combination with each other, and/or in combination with other techniques. Further, other techniques for creating a lack of symmetry in the mesa may also be used, such as a non-uniform temperature distribution inside the mesa.

Figure 8:
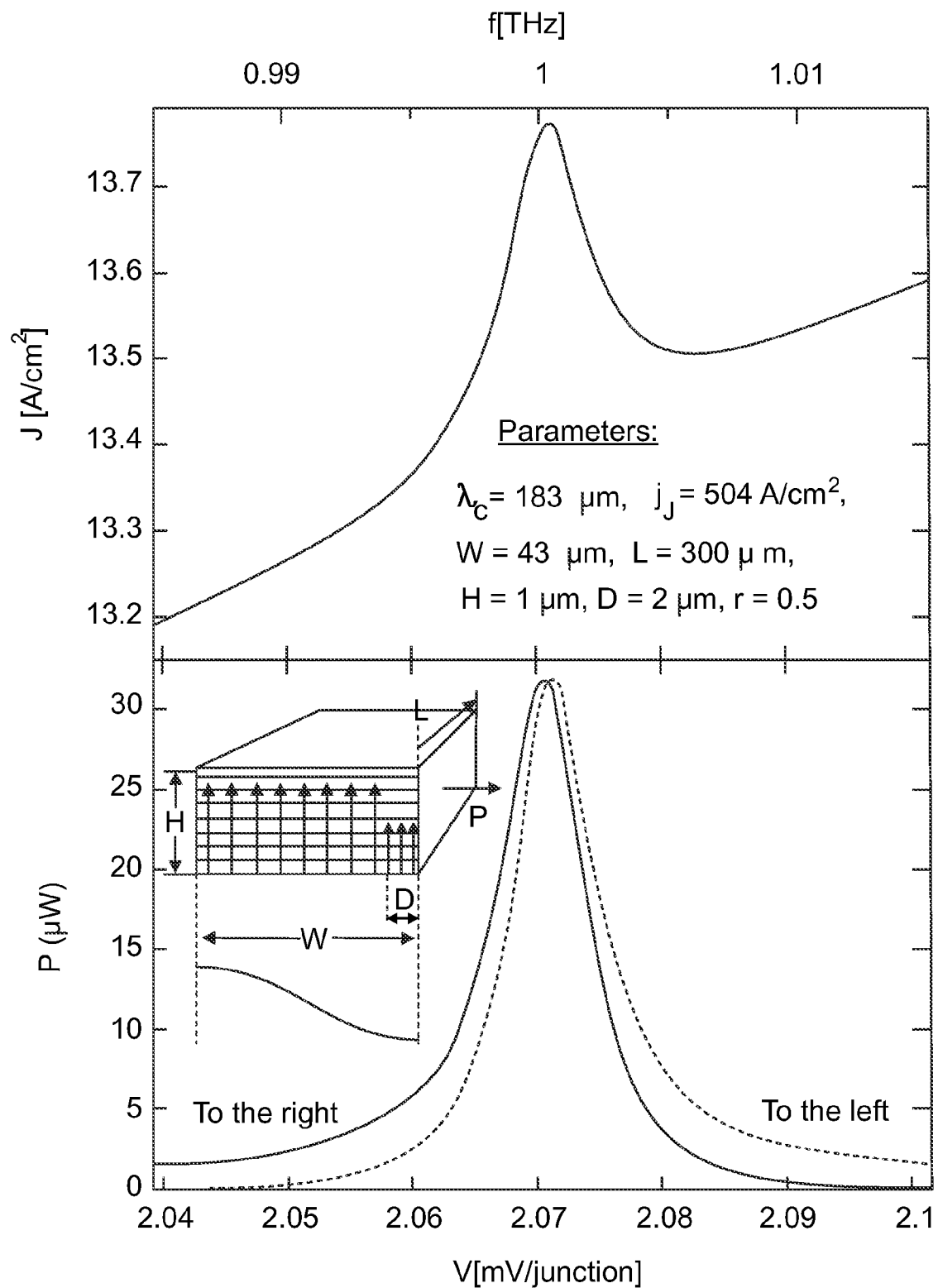
FIG. 8 illustrates computed current-voltage characteristic and radiation power for an exemplary mesa with modulated critical current. Geometry, current modulation, and excited cavity mode are illustrated in the inset. The used superconducting and geometrical parameters are listed in the upper plot, where $\lambda_c$ is the c-axis London penetration depth and $j_J$ is the Josephson critical current in the main part of the mesa.
Figure 9A:
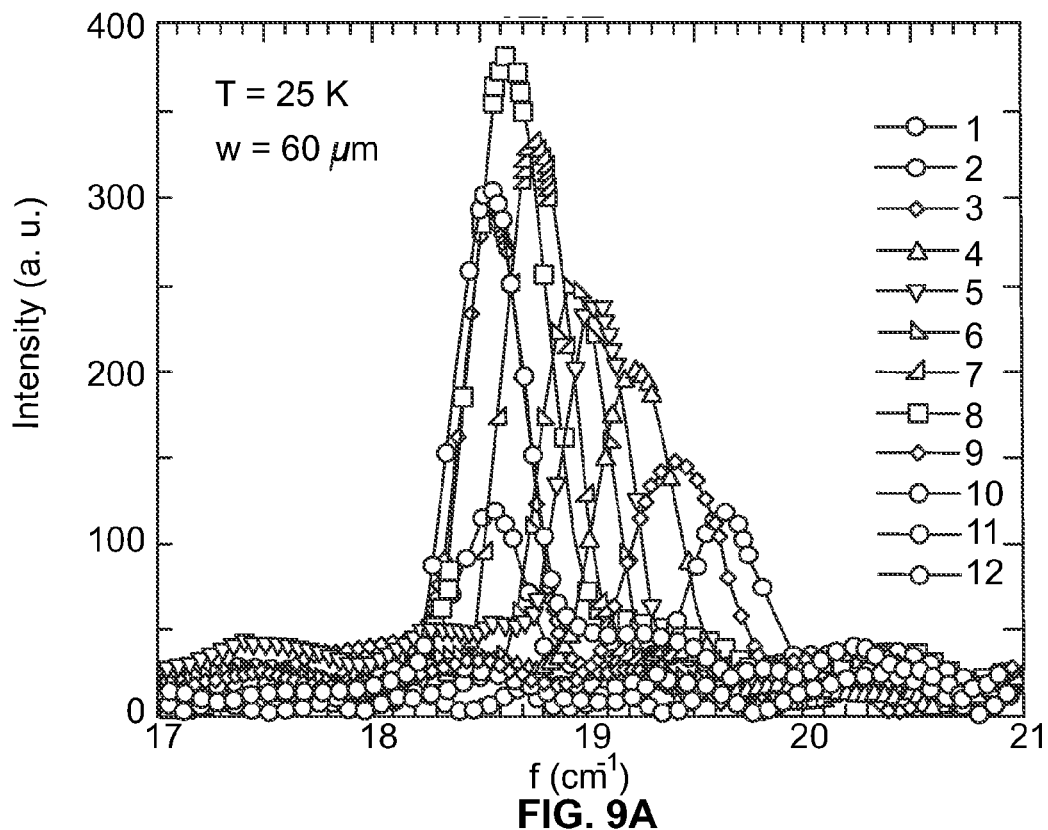
FIGS. 9A and 9B illustrate the tunability of the emitted radiation from an exemplary 60 μm wide mesa. (9A) emission spectra for several bias voltages that are identified in panel (9B) showing the voltage dependence of the emitted radiation power.
Figure 9B:
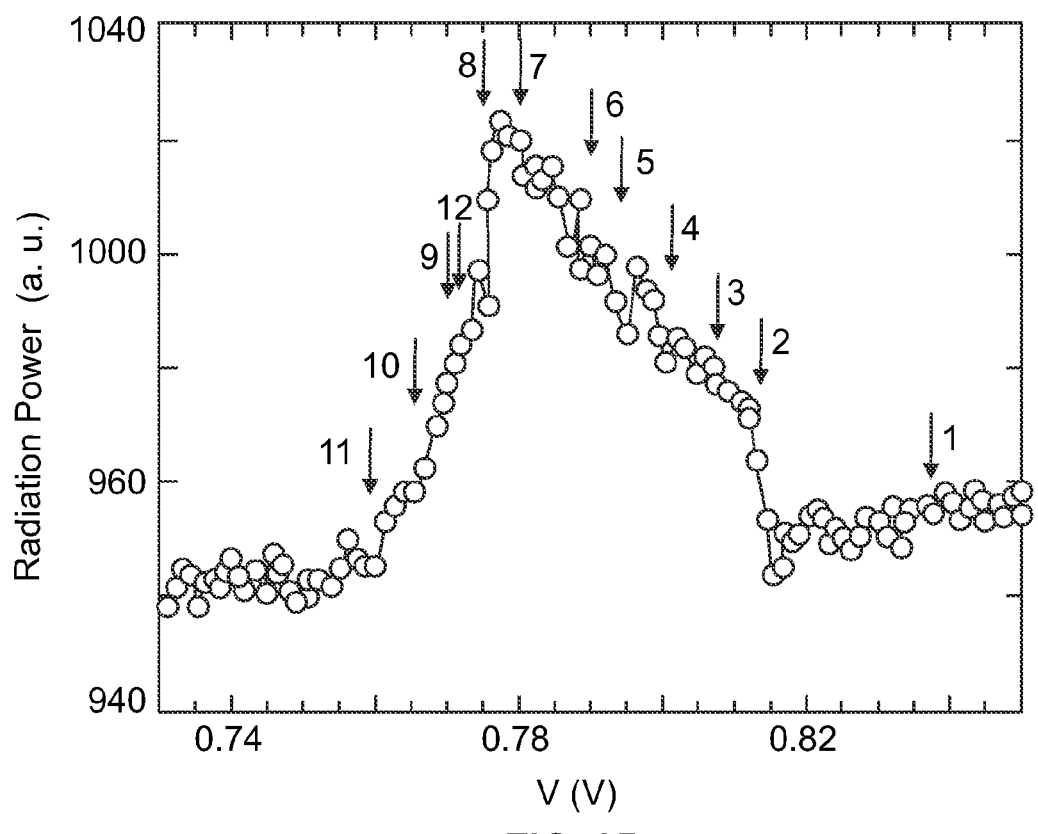

In one embodiment, superconductivity may be suppressed within a narrow region of width D near an edge of mesa structure. Such suppression may either spontaneously appear during fabrication processes or can be deliberately introduced by irradiation or heat treatments. FIG. 8 illustrates the computed current-voltage characteristics and radiation from both sides of mesa structure 26 in the vicinity of the resonance for representative mesa parameters. The mesa width, W=43 μm, is selected to bring the resonance frequency close to 1 THz; and we assume that within the distance D~2 μm from the edge the critical current is half the bulk value, which we assume to be 504 A/cm². These and other parameters are listed in the upper plot.

For selected mesa parameters, the power reaches 30 μW in the maximum and the power-conversion efficiency in the maximum is about 3%. Both the radiation power and efficiency can be further increased by increasing the modulation depth, D.

The above analysis suggests that for the same superconducting parameters, the optimum modulation depth is reached for D~W/2 yielding the maximum radiation power of around 2 mW for $L_y$~300 μm. Increasing the length $L_y$ of the mesa increases the radiation power in proportion.

The radiation source 10 of FIG. 1 may include any number of other components. For example, the source 10 may include contacts 18,20 (e.g. contacts formed from gold) in contact with a crystal 16. Contacts 18,20 are connected to a power source via lead wires 22,24. Source 10, also includes a conductive (e.g. gold) layer over the structure 26 that is in contact with a lead wire 30. An electrically insulating (e.g. $CaF_2$) material 32 may be placed over the structure 26 to isolate structure 26 and/or layer 28 from other parts of source 10.

The radiation source 10 may be an all solid state source with no moving parts. In many embodiments, the source 10 may be portable. For example, in some embodiments, the source 10 may have a volume, incrementally, of less than about 10 cubic meters, less than 1 cubic meter, less than 1000 cubic cm, less than 100 cubic cm, less than 10 cubic cm, less than 1 cubic cm, less than 500 cubic mm, less than 250 cubic mm, less than 150 cubic mm, less than 100 cubic mm, less than 75 cubic mm, less than 50 cubic mm, less than 25 cubic mm, less than 20 cubic mm, less than 15 cubic mm, less than 10 cubic mm, less than 5 cubic mm, less than 3 cubic mm, less than 1 cubic mm, less than 0.5 cubic mm, less than 0.1 cubic mm. As another example, in some embodiments, the radiation source 10 may have an incremental weight of less than about 100 kg, less than 10 kg, less than 1 kg, less than 500 g, less than 100 g, less than 50 g, less than 25 g, less than 15 g, less than 10 g, less than 5 g, less than 2 g, less than 1 g, less than 500 mg, less than 250 mg, and/or less than 150 mg.

Radiation source 10 may also include other components, such as components used to enhance the emission efficiency of radiation source 10. For example, radiation source 10 may include one or more antennas (e.g. bow-tie antennas), impedance matching dielectric coatings and/or gratings configured to facilitate transmission of radiation from source 10. Further, source 10 may include multiple structures 26 arranged on crystal 16.

Radiation source 10 may be configured to provide a THz radiation wave (e.g. may be configured to provide radiation that is at a frequency in a range of about $3 \times 10^{11}$ Hz to about $3\times10^{12}$ Hz). In some embodiments, radiation source 10 may be configured to provide radiation having a frequency of at least about 0.1 THz, at least about 0.2 THz, at least about 0.3 THz, at least about 0.5 THz, at least about 0.75 THz, at least about 1 THz, at least about 1.5 THz, at least about 2 THz, and/or at least about 2.5 THz. In some embodiments, radiation source 10 may be configured to provide radiation at a frequency that is no more than about 10 THz, no more than about 6 THz, no more than about 3 THz, no more than about 2.5 THz, no more than about 2 THz, no more than about 1.5 THz, no more than about 1 THz, no more than about 0.75 THz, and/or no more than about 0.5 THz.

In some embodiments, the radiation source 10 may be tunable. In some embodiments, the radiation source 10 may be tunable by at least about 3% (e.g. a 3% deviation on either side of the median frequency provided by the source 10), by at least about 5%, by at least about 7%, and/or by at least about 9%.

The radiation source 10 based on superconductors may be configured to operate in any of various temperatures. In some embodiments, the radiation source 10 is at least configured to be capable of providing THz radiation at a temperature of 20 K, 30 K, 40 K, 50 K, 60 K, 70 K, 80 K, 90K, 105 K, and/or 120 K. The upper limit may be provided by superconducting transition temperature of a material used to form source 10 (e.g. 90 K for $Bi_2Sr_2CaCu_2O_8$ and 124 K for $Bi_2Sr_2Ca_2Cu_3O_{10}$). In some embodiments, the radiation source 10 may be configured such that it does not provide THz radiation above a particular temperature. In some embodiments, the radiation source 10 may be configured such that it does not provide THz radiation at temperature above 200 K, above 150 K, above 100 K, above 75 K, and/or above 60 K.

Figure 2:
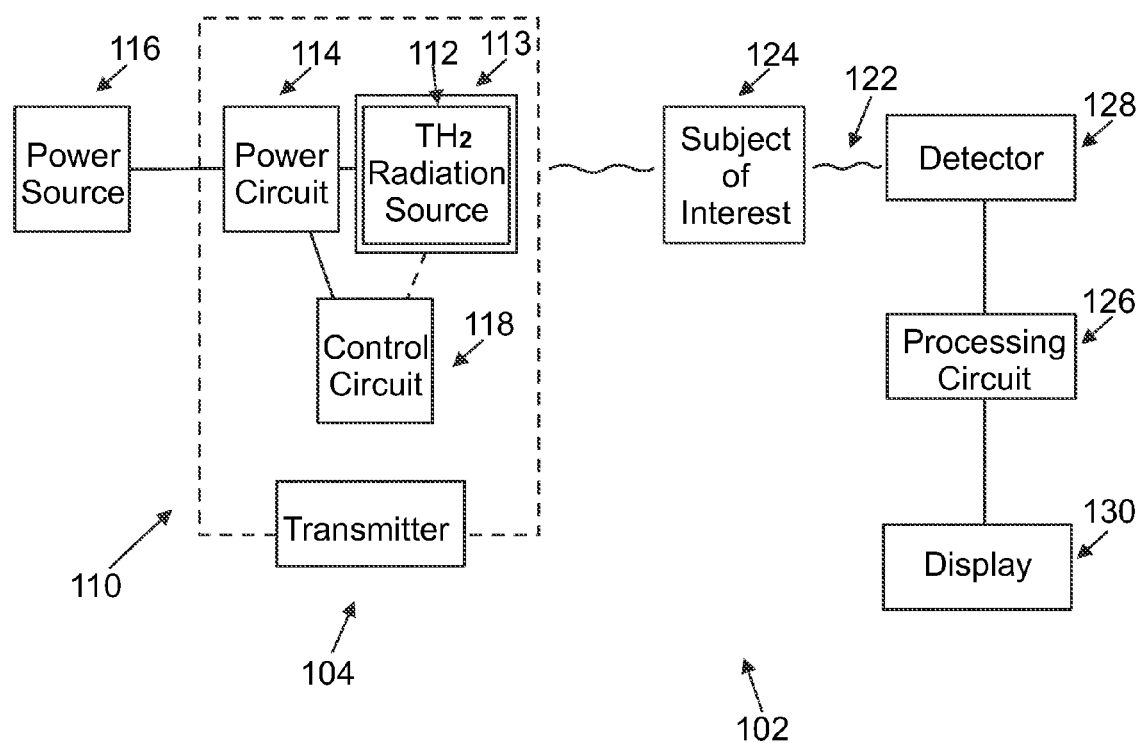
FIG. 2 is a system diagram incorporating a source of THz radiation according to one embodiment.

Referring to FIG. 2, in one exemplary embodiment, a THz-based detection system 102 includes a housing 110 configured to contain a radiation source 112 such as radiation source 10 (FIG. 1). The housing 110 also contains a power circuit 114 configured to connect the radiation source 112 to an external power source 116 (e.g. an AC power source), and a control circuit 118 configured to control application of power from the power source 116 to the radiation source 112.

The housing 110 may be configured to be portable. For example, the housing 110 may have incremental volumes of less than about 200 cubic ft, less than 150 cubic ft, less than 100 cubic ft, less than 75 cubic ft, less than 50 cubic ft, less than 25 cubic ft, less than 20 cubic ft, less than 15 cubic ft, less than 10 cubic ft, less than 5 cubic ft, less than 3 cubic ft, and/or less than 1 cubic ft. The portion (e.g. transmitter 104) of system 102 contained by housing 110 may have a weight of less than about 100 kg, less than 50 kg, less than 25 kg, less than 15 kg, less than 10 kg, less than 5 kg, less than 2 kg, less than 1 kg, less than 500 g.

The housing 110 may also include other components to affect a direction in which radiation is provided by the THz radiation transmitter 104 of system and/or a wavelength of radiation provided from the transmitter 104. For example, the housing 110 may house one or more of a shield, a filter, a reflector, etc. The housing 110 may also include a means 113 of maintaining the radiation source 112 in a superconducting state, such as a cryo-cooler and temperature controller.

The system 102 also includes a detector 120 configured to detect THz radiation 122 that has interacted with a subject of interest 124. The subject of interest 124 may be a biological subject such as a person, an inanimate object such as an object to be screened by a security screening system, etc. The detector 128 provides an output to a processing circuit 126 that is configured to process data provided from the detector 128. The processing circuit 126 may be configured to process data from the detector 128 to provide information useful in providing diagnostic information. In other embodiments, the processing circuit 126 may be configured to process data from the detector 128 to provide information relating to the contents of the subject of interest 124. The processing circuit 126 may be connected to a display 130 such that information based on data processed by the circuit 126 may be displayed to a user of the system 102. The processing circuit 126 may be a common circuit with the control circuit 118. Further, the housing 110 may be configured to house one or more of the display 130, the detector 128, and the processing circuit 126.

EXAMPLES

The following examples are presented to illustrate the present invention and to assist one of ordinary skill in making and using the same. The examples are not intended in any way to otherwise limit the scope of the invention.

Example 1

A structure was formed as shown in FIG. 1 using a BSCCO crystal as a base onto which a BSCCO mesa was formed. The mesa had a typical size of $300\times80\times1$ $\mu m^3$.

Figure 3:
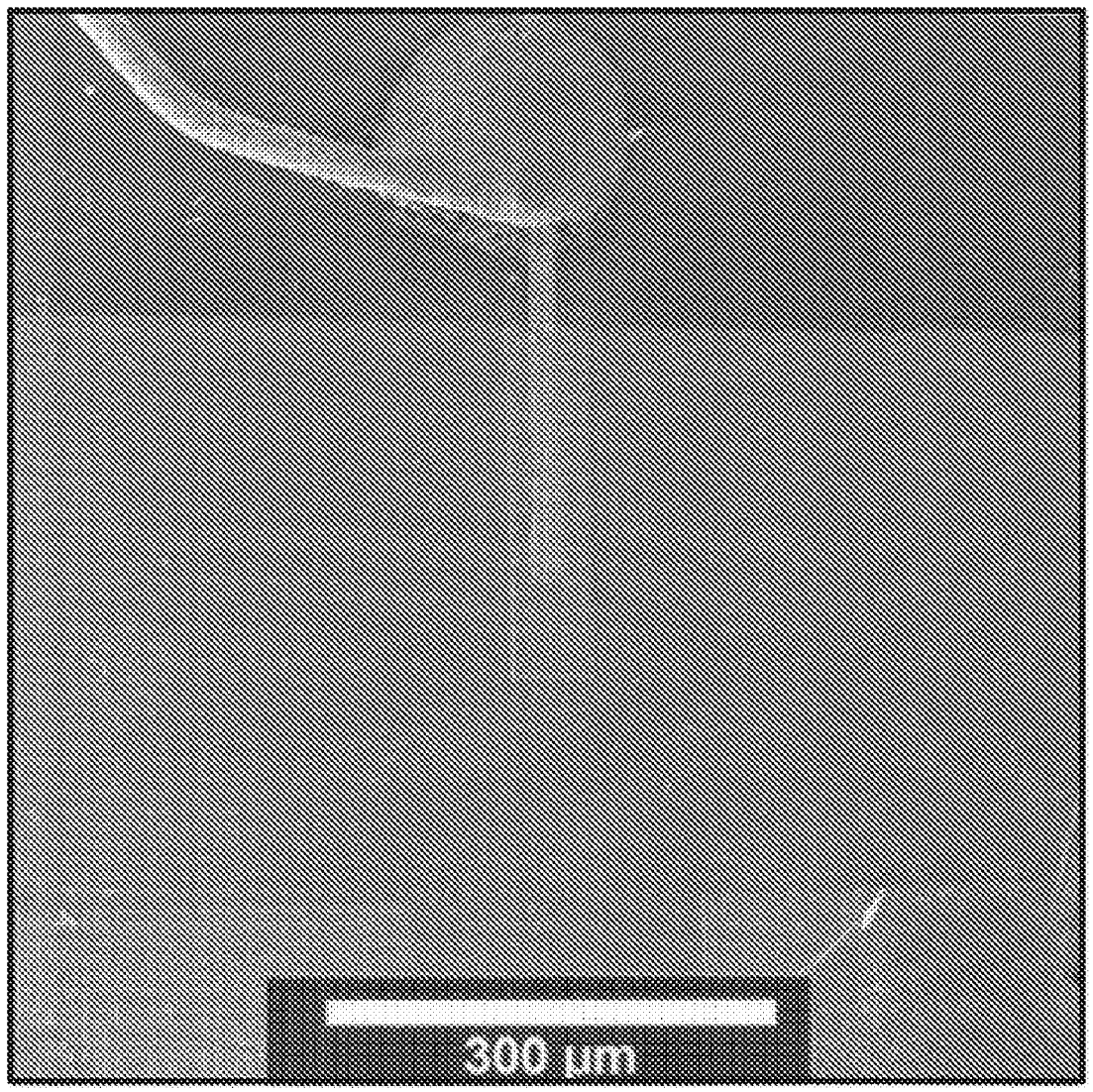
FIG. 3 is a SEM image of a THz-source in the embodiment shown in FIG. 1.

The structure was formed by:

annealing a BSCCO single crystal to establish the desired value of $T_c$;

Cleaving the crystal 16 parallel to the $CuO_2$-planes to expose a clean surface;

Coating this exposed surface with an Au-film, typically about 100 nm thick;

Defining the mesa structure 26 and electrical contacts 18,20 using photolithography according to a lay-out as shown in FIG. 1 (results on mesas with variable width W and fixed length of 300 $\mu$m were created);

Using the photoresist portion from the previous step as a mask, the mesa structure 26 is fabricated by removing the surrounding BSCCO material using Ar-ion milling (a typical mesa height is 1 $\mu$m. By adjusting the incident angle of the Ar-ions, mesa structures 26 with different cross-sections can be fabricated. For example, the scanning electron microscope (SEM) image in FIG. 3 displays a mesa structure 26 having a trapezoidal cross-section with one side-face sloped steeper than the other);

After removal of the photoresist portion, coating the lower part of the crystal 16 with an insulating layer of $CaF_2$ 32 through a shadow mask; and depositing an Au-strip 28 through a shadow mask to establish electrical contact to the top of the mesa structure 26.

Example 2

An electromagnetic cavity resonance was excited in the BSCCO structure of Example 1. A current passed down the mesa excites the fundamental cavity mode on the width of the mesa as indicated by the solid half-wave, and high-frequency electromagnetic radiation is emitted from the side faces. We analyze the spectral properties of the radiation with a set of parallel-plate metal waveguide filters. These filters have a cut-off for electromagnetic waves whose E-field is parallel to the metal sheets (TE-waves) whereas there is no cut-off for TM-waves. The cut-off frequency for the $1^{st}$ TE-mode is given by $f_c=c_0/2d$, where d is the spacing between the metal plates and $c_0$ is the vacuum speed of light, meaning that TE-polarized waves with frequency below $f_c$ are not transmitted. In the following, parallel filter setting refers to the filter plates aligned with the $CuO_2$-planes.

The sample is mounted in a He-gas flow cryostat equipped with a Teflon window, and the emitted power is detected with an ac-coupled Si-composite bolometer located at about 20 cm from the sample. Unwanted far-IR radiation is rejected with a 3 THz-low pass filter.

Excitation of the structure of Example 1 established synchronized in-phase oscillations of the junctions thereby enabling continuous-wave coherent radiation power of up to ~50 nW at ~0.6 THz when measured by a remote detector.

These values are more than 10,000 times larger than any reported far-field power levels. The devices operate in zero applied magnetic field.

Figure 6:
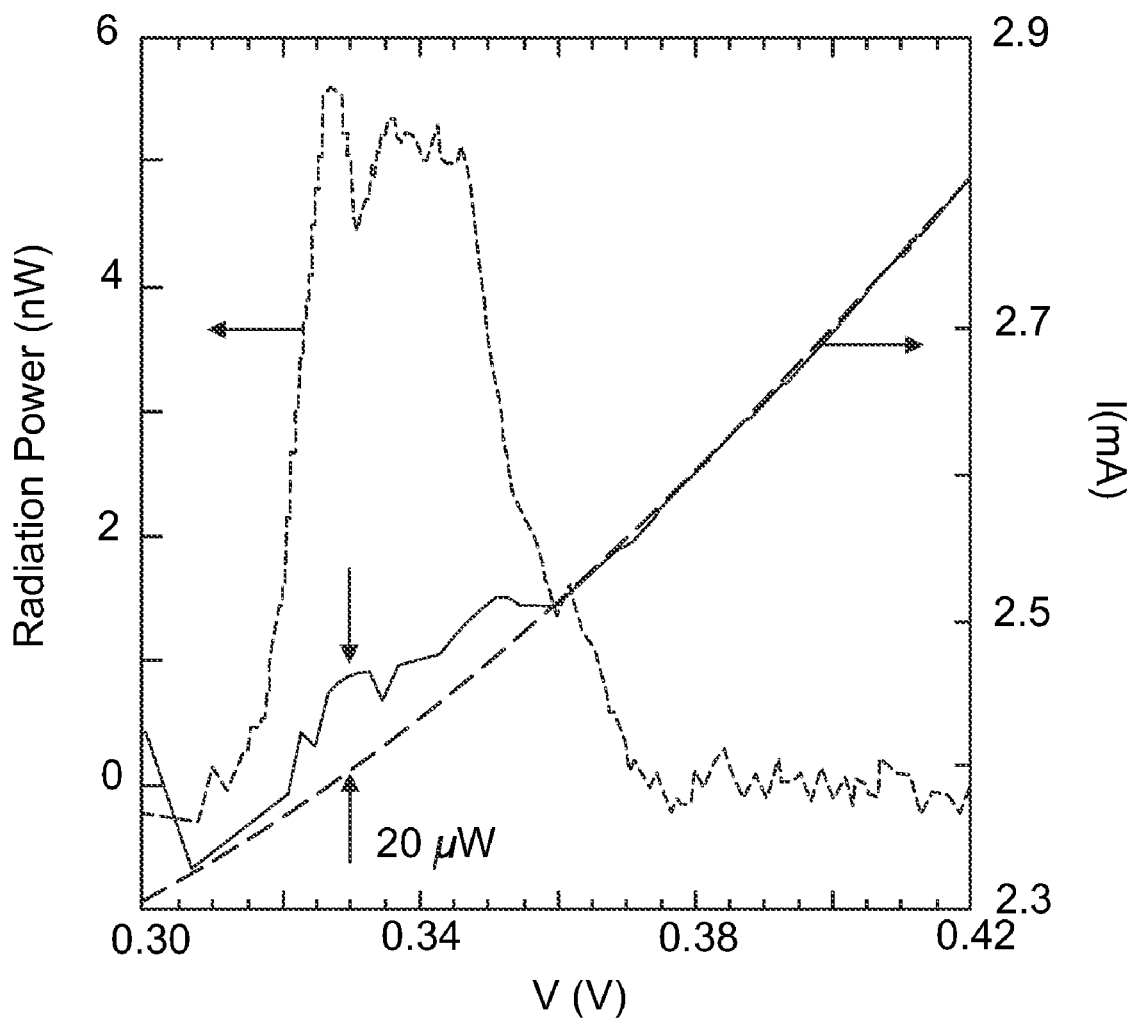
FIG. 6 illustrates the voltage dependence of the emission power (left y-axis) and of current (right y-axis). The excess current associated with the emission indicates that 20 μW of power are pumped into the cavity resonance for an exemplary embodiment.

The available power is potentially much larger, as there is evidence that up to 20 µW of power are pumped into the observed THz cavity resonance (see FIG. 6).

Example 3

Figure 4A:
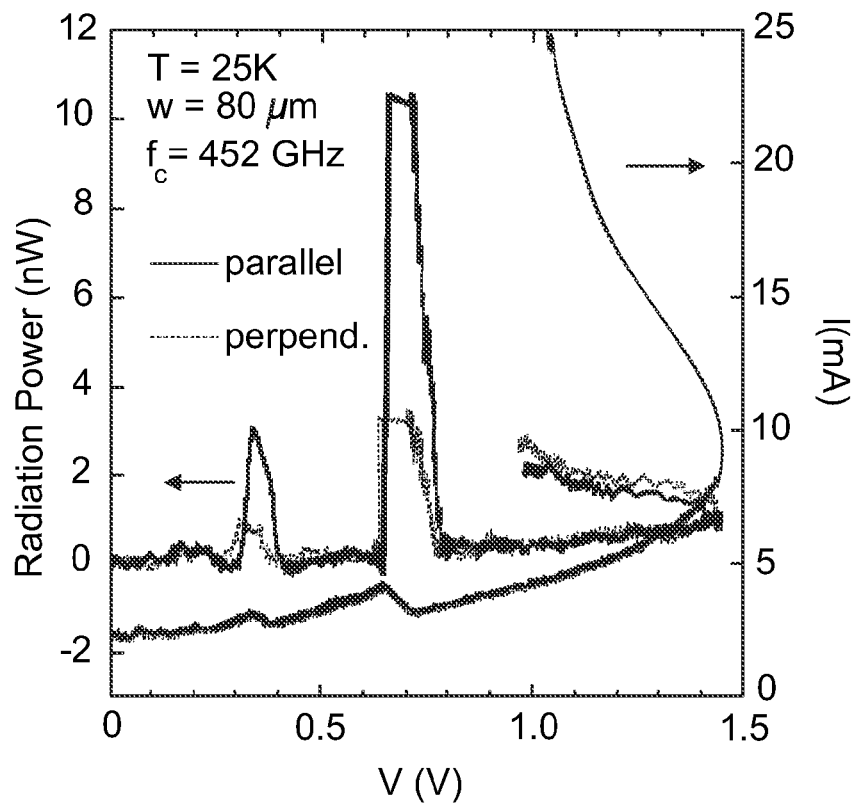
FIG. 4A illustrates the voltage dependence of the current (right y-axis) and of the radiation power (left y-axis) for parallel and perpendicular settings of the filter with 0.452 THz cut-off frequency. The data are taken on decreasing voltage bias. Polarized Josephson emission occurs at 0.71 and 0.37 V with a peak power of 11 nW.
Figure 4B:
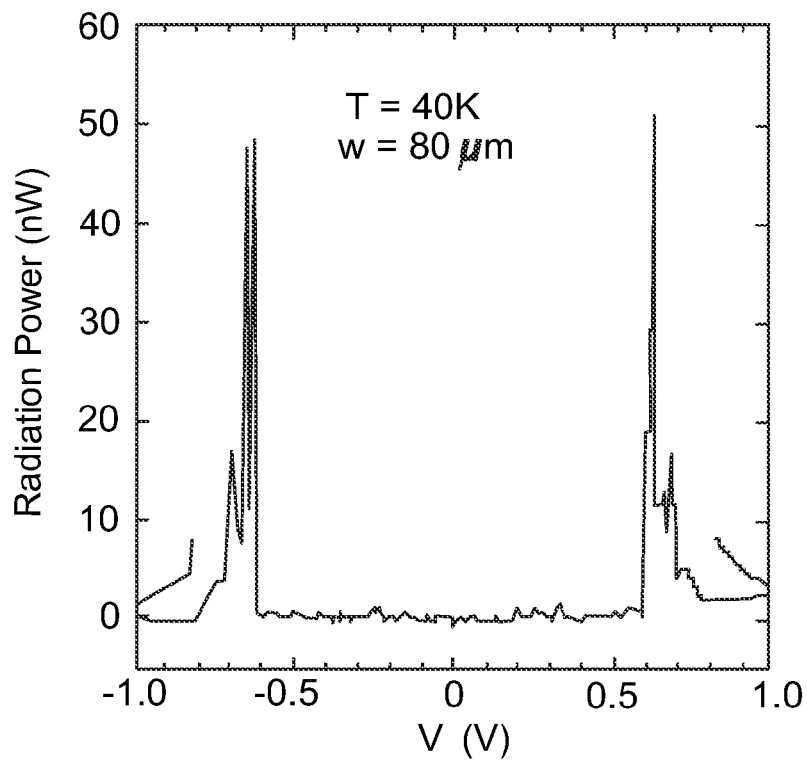
FIG. 4B illustrates the detected THz radiation power from a 80 μm wide mesa versus applied voltage.

FIG. 4A shows the voltage dependence of the return branch of the IV-characteristics (IV-c) and the radiation power detected simultaneously by the bolometer for the parallel and perpendicular filter settings (see FIG. 1), respectively; on increasing bias the IV-c displays the typical sequence of quasiparticle branches without any detectable emission. These results are obtained in zero applied magnetic field. Data for parallel and perpendicular filter setting identify peaks of polarized Josephson radiation near 0.37 V and 0.71 V, and un-polarized thermal radiation at high current and voltage bias. The peak power in FIG. 4A is around 11 nW, and we recorded radiation powers up to 50 nW when no filters are inserted into the beam path (FIG. 4B). These values are more than 10,000 times larger than previous reports of far-field radiation extracted from BSCCO-mesas. Furthermore, upon rotating the cutoff filter, both peaks decrease in the same proportion indicating the same radiation frequency.

Figure 5A:
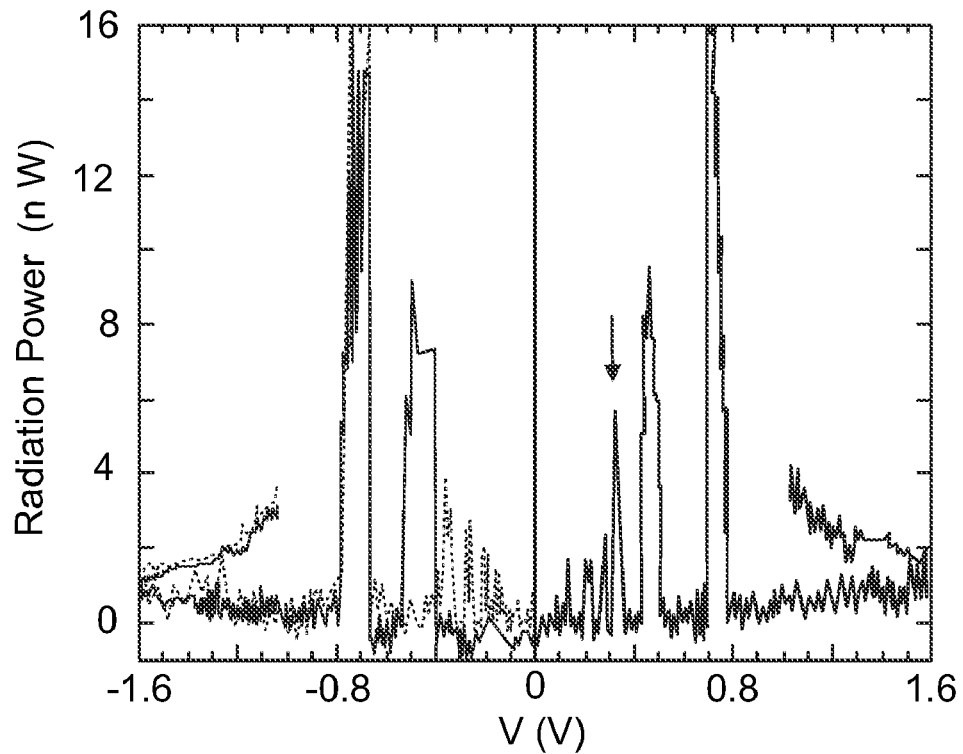
FIGS. 5A and 5B illustrate the coherent nature of radiation emitted by an exemplary power source consisting of a 80 μm wide mesa.
Figure 5B:
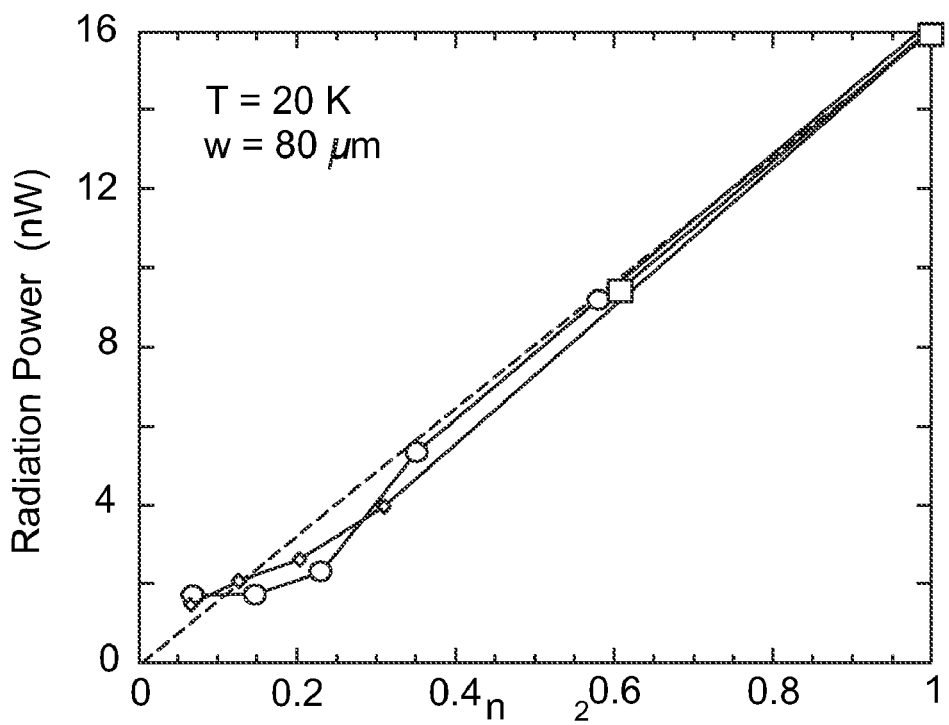

The jumps in the return branch of the IV-c, that often correlate with the radiative peaks, indicate that a fraction of the junctions in the mesa revert to the non-resistive non-radiative supercurrent state. This allows evaluation of the radiation from the same sample for varying numbers of emitters, and thereby obtaining a direct test of coherency. FIG. 5A displays a sequence of emission peaks for positive and negative bias voltages on the 80-µm mesa. The number of active junctions, $n_{rel}$, relative to the highest emission peak, can be determined directly from the IV-c. Equivalently, since successive peaks correspond to the same emission frequency (see FIG. 4A) $n_{rel}$ can be estimated also from the voltages of the emission. The observed peak powers are proportional to $n_{rel}^2$ as shown in FIG. 5B. This demonstrates that the junctions in the stack emit coherently.

Example 4

FIG. 6 shows a close-up of the return branch of IV-c and of the radiation power of the $3^{rd}$ peak in FIGS. 5A&B. The absence of a jump in the IV-c allows to establish a baseline of the current and to determine the excess current that is associated with the emission. These data suggest that about 20 µW—roughly 2.5% of the total dc-power dissipated in the mesa—are pumped into the in-phase cavity resonance, implying that significantly enhanced radiation powers could be obtained with this mesa, for example through improved impedance matching with the help of antennas, gratings or dielectric coatings, and/or through more efficient collection techniques using focusing elements.

Example 5

Figure 7A:
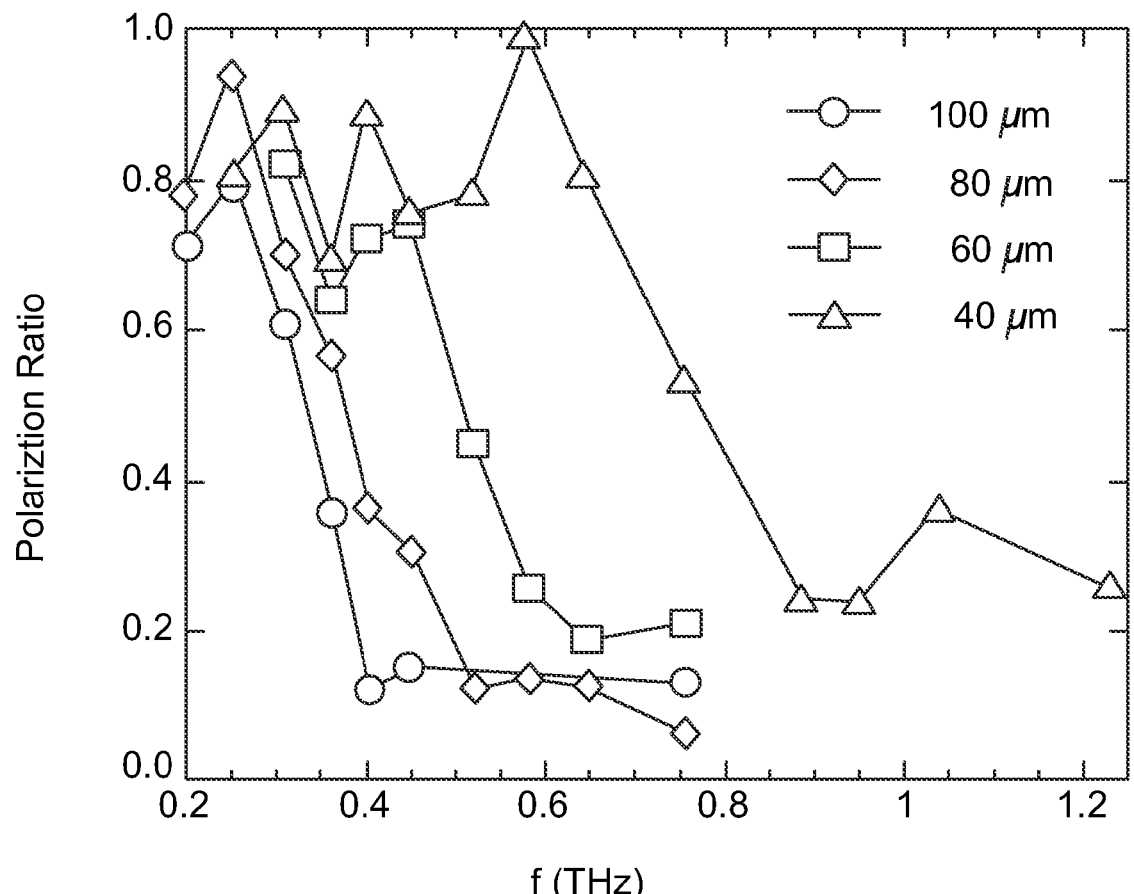

The spectral characterization of the detected radiation is presented in FIG. 7. These data enable an estimation of the radiation frequency as that filter cut-off frequency where the polarization ratio levels off, i.e., 0.4, 0.52, 0.64 and 0.85 THz for the 100-µm, 80-µm, 60-µm and 40-µm wide mesas, with ~10% uncertainty. Moreover, for the first three mesas these frequency values were confirmed by direct measurements of spectra shown in FIG. 7B. These values are in good agreement with the frequency, f=c/2nw, expected for the fundamental cavity resonance with length w, yielding f=0.42 THz for w=100 µm, where n≈3.5 is the far-IR refractive index of BSCCO for c-axis polarized waves.

Furthermore, the observed radiation frequencies increase in proportion to 1/w demonstrating that they correspond to the fundamental cavity resonance (see inset of FIG. 7). To excite this mode, the Josephson frequency across each junction, f=2e/h $V_{jet}$ must match the cavity resonant frequency, where e is the elementary charge, h is Planck's constant, and $V_{jet}$ the voltage per junction.

Using the mesa height of 1.1 µm from AFM, the 1.56 nm spacing of $CuO_2$-planes and assuming that all junctions contribute equally, the mesa voltage shown in FIG. 4A for the large radiative peak corresponds to 0.49 THz, that is in good agreement with the filter spectral data. Thus, on decreasing bias from the fully resistive state the emission power builds up as the Josephson frequency comes in resonance with the cavity.

During a jump in the IV-c the number of resistive junctions decreases and the current and therefore the voltage per remaining junction increase. Consequently, the Josephson frequency increases, falls out of resonance with the cavity mode, and emission ceases. With further decreasing bias the resonance is again approached from above, and the behavior repeats yielding a second emission peak.

Scaling the size and/or shape of the BSCCO crystals may lead to further enhancements of emission frequencies and/or power levels.

Illustrative Embodiments

One embodiment is directed to a solid-state source of THz radiation comprising a layered superconductor for providing coherent and polarized THz radiation.

Another embodiment is directed to a THz radiation source comprising a large number of stacked Josephson junctions configured to have a Fabry-Perot cavity resonance to synchronize the junctions. The radiation source may provide coherent enhancement of the radiation intensity using the Fabry-Perot cavity resonance.

Another embodiment is directed to a THz radiation source that does not require application of a magnetic field to generate the THz radiation. The THz radiation source may include a superconducting material. The superconducting material may include one or more Josephson junctions, and one or more of the junctions may be an intrinsic Josephson junction.

Another embodiment is directed to a THz radiation source. The THz radiation source is configured to excite high-frequency electro-magnetic waves by creating a non-uniform Josephson critical current density. In some embodiments, the non-uniform coupling constant is created by use of one or more of a compositional gradient and a non-uniform shape.

Another embodiment is directed to a THz radiation source comprising a cavity. The emission frequency of the radiation source is tunable based on the cavity size.

Another embodiment is directed to a source of THz radiation. The THz radiation source comprises a superconductor configured to emit THz radiation. The superconductor may include one or more Josephson junctions. One or more of the Josephson junctions may be intrinsic Josephson junctions. The superconductor may be configured to emit THz radiation without an application of an external magnetic field.

Another embodiment is directed to a system comprising a radiation source as disclosed in any of the illustrative embodiments discussed above, and a detector configured to provide information based on an interaction of THz radiation from the radiation source with a subject of interest.

Another embodiment is directed to a detection system that includes a solid-state, portable source of THz radiation. The system also includes a detector configured to provide information based on an interaction of THz radiation from the radiation source with a subject of interest.

Coherent electromagnetic waves at THz-frequencies hold promise for noninvasive sensing, imaging and spectroscopy across the physical, medical and biological sciences. The embodiments discussed above may be applied to diagnosis and/or evaluation applications such as medical diagnostics, space exploration, environmental monitoring, security screening, manufacturing evaluation, and/or pharmaceutical evaluation. The wavelength range of 30 μm to 1 mm may allow for imaging with good spatial resolution.

The embodiments discussed above may also be applied to other applications such as data communication applications (e.g. high-speed data communication applications). For example, a system may include a transmitter comprising a THz radiation source, the transmitter potentially being configured to encode a THz transmission with data; a communication medium (e.g. open space such as through the environment, a body capable of carrying THz radiation, etc.); and a receiver configured to receive the THz radiation that was sent along the medium, and/or to decode data carried by the THz radiation.

The source of THz waves for any of these applications may be a powerful, all-solid state source.

The foregoing description of embodiments of the present invention has been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A detection system, comprising:
a solid-state, portable source of THz radiation wherein the source of the THz radiation is configured to provide at least one of (a) about 30 nW of THz radiation, and (b) THz radiation without an application of an external magnetic field; and
a detector configured to provide information based on an interaction of THz radiation from the radiation source with a subject of interest.

2. A source of THz radiation, comprising:
a superconductor, the superconductor configured to emit THz radiation in response to an applied current and without an application of an external magnetic field,
wherein the source is configured to emit at least 30 nW of THz radiation.

3. The source of claim 2, wherein the superconductor comprises at least one Josephson junction.

4. The source of claim 3, wherein the at least one Josephson junction is an intrinsic Josephson junction.

5. The source of claim 4, wherein the superconductor comprises a layered high-temperature cuprate.

6. The source of claim 5, wherein the layered high-temperature cuprate comprises $Bi_2Sr_2CaCu_2O_8$.

7. The source of claim 2, wherein the superconductor comprises a multiplicity of intrinsic Josephson junctions.

8. The source of claim 2, wherein the superconductor comprises a mesa.

9. The source of claim 8, wherein the mesa is located on a crystal formed from the superconductor.

10. The source of claim 8, wherein the mesa is configured such that a plurality of Josephson junctions oscillate at essentially a same frequency and essentially in phase.

11. The source of claim 8, wherein the mesa is configured to include a non-uniform Josephson critical current density for inducing efficient coupling between a current applied to the superconductor and electromagnetic modes of the superconductor.

12. The source of claim 11, wherein the non-uniform Josephson critical current density is caused at least in part by a non-uniform shape of the mesa.

13. The source of claim 11, wherein the non-uniform Josephson critical current density is caused at least in part by a compositional gradient in the mesa.

14. The source of claim 2, wherein a frequency at which the THz radiation is provided is tunable.

15. The source of claim 2, wherein the source is portable.

* * * * *